(12) United States Patent
Haase et al.

(10) Patent No.: US 11,678,855 B2
(45) Date of Patent: Jun. 20, 2023

(54) REGISTRATION AND COMPARISON OF MEASURED AND SIMULATED INTRACORONARY PULLBACK CURVES

(71) Applicant: KONINKLIJKE PHILIPS N.V., Eindhoven (NL)

(72) Inventors: Christian Haase, Hamburg (DE); Michael Grass, Buchholz in der Nordheide (DE); Martijn Anne Van Lavieren, Abcoude (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 464 days.

(21) Appl. No.: 16/645,224

(22) PCT Filed: Sep. 6, 2018

(86) PCT No.: PCT/EP2018/073916
§ 371 (c)(1),
(2) Date: Mar. 6, 2020

(87) PCT Pub. No.: WO2019/048508
PCT Pub. Date: Mar. 14, 2019

(65) Prior Publication Data
US 2020/0289078 A1    Sep. 17, 2020

(30) Foreign Application Priority Data
Sep. 8, 2017  (EP) ..................... 17190022

(51) Int. Cl.
*A61B 6/00*     (2006.01)
*G16H 50/50*    (2018.01)
(Continued)

(52) U.S. Cl.
CPC .......... *A61B 6/5247* (2013.01); *A61B 5/0215* (2013.01); *A61B 6/461* (2013.01);
(Continued)

(58) Field of Classification Search
None
See application file for complete search history.

(56) References Cited

U.S. PATENT DOCUMENTS

2015/0131886 A1*  5/2015  Aben ................. G06T 7/32
                                                382/132
2017/0032097 A1*  2/2017  Itu .................... G16H 50/50

FOREIGN PATENT DOCUMENTS

EP      2942006 A1     11/2015
WO   2016087396 A1      6/2016
(Continued)

OTHER PUBLICATIONS

International Search Report and Written Opinion, International Application No. PCT/EP2018/073916, dated Oct. 22, 2019.

*Primary Examiner* — Jonathan Cwern (57) ABSTRACT

An apparatus for analyzing coronary vessels and a corresponding method are provided in which simulated pullback data obtained from (non-invasively) acquired diagnostic images is co-registered with invasively acquired intravascular pullback data and the co-registration is used to identify disparities in the pullback data obtained using the two modalities. These disparities allow for deriving further information about the vessel geometry and/or the blood flow through the vessel. They may therefore be used to improve the physiological model.

16 Claims, 4 Drawing Sheets (51) Int. Cl.
*G16H 30/20* (2018.01)
*G16H 50/30* (2018.01)
*G16H 50/20* (2018.01)
*G16H 30/40* (2018.01)
*A61B 5/0215* (2006.01)
*A61B 5/055* (2006.01)

(52) U.S. Cl.
CPC .............. *A61B 6/504* (2013.01); *A61B 6/507* (2013.01); *A61B 6/5217* (2013.01); *G16H 30/20* (2018.01); *G16H 30/40* (2018.01); *G16H 50/20* (2018.01); *G16H 50/30* (2018.01); *G16H 50/50* (2018.01); *A61B 5/055* (2013.01); *A61B 6/481* (2013.01)

(56) References Cited

FOREIGN PATENT DOCUMENTS

| | | |
|---|---|---|
| WO | 2017055228 A1 | 4/2017 |
| WO | 2017076520 A1 | 5/2017 |
| WO | 2017076620 A1 | 5/2017 |

\* cited by examiner

REGISTRATION AND COMPARISON OF MEASURED AND SIMULATED INTRACORONARY PULLBACK CURVES

CROSS-REFERENCE TO PRIOR APPLICATIONS

This application is the U.S. National Phase application under 35 U.S.C. § 371 of International Application No. PCT/EP2018/073916, filed on Sep. 6, 2018, which claims the benefit of European Patent Application No. 17190022.8, filed on Sep. 8, 2017. These applications are hereby incorporated by reference herein.

FIELD OF THE INVENTION

The present invention relates to an apparatus for analyzing coronary vessels of a patient, a corresponding method and a respective computer program. In particular, the present invention relates to an improved analysis of a vessel of interest of the coronary physiology employing a comparison of simulated pullback data of the vessel of interest with intravascular pullback data that has been obtained in-situ from the vessel of interest.

BACKGROUND OF THE INVENTION

Functional stenosis severity in coronary arteries is typically assessed by considering the ratio of the pressure distal the stenosis (Pa) to the pressure in the aorta (Pa). This ratio may particularly be regarded using Fractional Flow Reserve (FFR) or instantaneous wave-Free Ratio (iFR), which are both determined from said pressure ratio. FFR measurements use whole-cardiac cycle pressure traces and have to be performed in a state of hyperemia, typically induced by the administration of vasodilatory agents. In contrast, iFR measurements are performed at rest during a specific period of the cardiac cycle, namely the diastole, which is also referred to as the wave-free period. Calculations of these indices can be performed on a single location in a coronary artery or along the longitudinal axis of the vessel.

In the past, the determination of coronary artery disease along the longitudinal axis of the coronary vessel has been performed using an invasive procedure in which a pullback of a pressure sensor equipped guide wire through a vessel of interest was performed, thereby determining the intravascular pressure tracing of the pressure at a plurality of locations along said vessel of interest. On the basis of this intravascular pressure tracing, the progression of the FFR or iFR could be determined along the longitudinal axis of the vessel.

In recent years, a so-called "virtual" approach has been developed, in which the fluid dynamics in the coronary vessels of a patient are simulated using a physiological model derived from non-invasively obtained diagnostic image data of the vessel of interest, i.e. image data acquired using medical imaging modalities, such as computed tomography (CT), magnetic resonance imaging (MRI), X-ray scanning or the like.

As an example, in order to determine virtual FFR/iFR, the pullback curve representing the pressure along the vessel of interest is estimated by simulating the fluid dynamics of the blood flow through said vessel using a respective fluid dynamics model as a part of the physiological model.

However, this fluid dynamics model may only be considered an estimation of the actual blood flow through the vessel of interest based on the diagnostic image data. As such, the reliability of the determination is highly dependent on the information that may be derived from the diagnostic image data.

SUMMARY OF THE INVENTION

In principle, the physiological model including the fluid dynamics model may be obtained on the basis of a single 2D diagnostic image. However, when using a single diagnostic image, effects such as foreshortening which are not visible in the angle chosen may occur, which may then result in incorrect conclusions with respect to the physiological model obtained from the 2D diagnostic image.

Furthermore, using respective boundary conditions such as blood viscosity or vessel wall composition, the fluid dynamics model may only estimate a somewhat idealized blood flow in the vessel of interest. In contrast, deviations in the blood flow, such as atypical blood flow rate or local blood flow turbulences are not properly presented in the fluid dynamics model.

So far, approaches in assessing functional stenosis severity in coronary arteries have been focused on using either an invasive method or an image-based "virtual" approach applying the physiological model. A combination of both approaches to obtain additional information about the vessel geometry and/or blood flow through the vessel has thus not been considered, since vessel foreshortening in the diagnostic image data and variations in the pullback speed of the pressure-wire during invasive measurements result in variations of the lengths of the pullback curves between the two modalities. Accordingly, the information obtained by both measurement methods is not compatible. It is therefore an object of the present invention to provide an improved apparatus and a corresponding method for analyzing coronary vessels.

It is a further object of the invention to provide an apparatus for analyzing coronary vessels of a patient, which allows retrieving additional information about the fluid dynamics within the vessel of interest. More particularly, it is an object of the present invention to provide an apparatus for analyzing coronary vessels that allows an adaption of the physiological model of patient in accordance with the patient's individual hemodynamic properties.

Accordingly, an apparatus for analyzing coronary vessels is provided which comprises an input unit adapted to receive simulated pullback data determined on the basis of a physiological model generated from at least one diagnostic image of a vessel of interest and intravascular pressure pullback data acquired in-situ from the vessel of interest. The apparatus further comprises a co-registration unit adapted to compare the simulated pullback data and the intravascular pullback data to identify at least one disparity between the simulated pullback data and the intravascular pullback data and to output the at least one disparity.

Therefore, an apparatus is provided which employs a co-registration of two different modalities for assessment of a vessel of interest. More particularly, the apparatus employs a combination of a (non-invasive) image-based physiological model with an invasive wire-based measurement of at least one hemodynamic parameter within the vessel of interest to obtain information about the vessel that would otherwise not be available.

In this context, the obtained hemodynamic parameter may in particular refer to the blood pressure. Thus, the wire-based measurement may in particular be a wire-based pressure measurement to obtain intravascular pressure pullback data. Likewise the physiological model may be used to obtain simulated pressure pullback data. Alternatively, other hemodynamic parameters may also be used, such as the vessel resistance to blood flow.

The at the least one diagnostic image used to generate the physiological model may particularly refer to at least one image representing the coronary vessels. More particularly, the at least one diagnostic image may represent a vessel tree including a vessel of interest of the heart. Hereby, the at least one diagnostic image may be acquired by means of a non-invasive diagnostic imaging modality, such as computed tomography (CT) or magnetic resonance imaging (MRI).

The non-invasive diagnostic imaging modality may hereby be gated. Such gated non-invasive diagnostic imaging modalities may typically employ a gated reconstruction, in which the acquisition of the at least one diagnostic image is performed in parallel with acquisition of data providing information over the cardiac cycle, such as electrocardiogram (ECG) or photoplethysmographic (PPG) data. This data is hereby used to gate the image acquisition and the reconstruction by means of respectively selected phase points of the cardiac cycle.

In an embodiment, the physiological model comprises a fluid dynamics model representing blood flow through the vessel of interest. This allows estimating, on the basis of the fluid dynamics model, the hemodynamic parameters in the vessel of interest. Accordingly, the fluid dynamics model allows for simulating pullback data for the vessel of interest.

In this context, the term pullback data generally relates to a plurality of hemodynamic parameter values determined at various positions along a longitudinal axis of a vessel of interest. Pullback data is obtained for a particular pullback length, which is defined as the distance between the starting position of the determination of the plurality of hemodynamic parameter values and the ending position of this determination. The pullback data may for example be used to determine the pressure gradient along the vessel of interest, which may be considered as a measure for stenosis severity.

In an embodiment, simulated pullback data may be determined by simulating the pullback using the fluid dynamics model. In this case, the distance between the starting point of the simulation and the ending point of the simulation may be considered the simulated pullback length.

Additionally, intravascular pullback data may be obtained using an invasive procedure, during which an interventional tool like a wire or a catheter for the measurement of the hemodynamic parameter is introduced into the vessel of interest.

The wire is then pulled from a distal end of the vessel to a proximal end of the vessel along a longitudinal axis of said vessel. During pullback, a plurality of intravascular hemodynamic parameter values are obtained for a plurality of intravascular positions along the longitudinal axis of the vessel of interest. Hereby, the distance between the starting position of the pullback recording at the distal end of the vessel of interest to the ending position of the pullback recording at the proximal end of the vessel of interest is called the intravascular pullback length.

The simulated pullback data and the intravascular pullback data are co-registered. Thus, for each one of the simulated values of the at least one hemodynamic parameter in the simulated pullback data is a corresponding one of the intravascular values of the at least one hemodynamic parameter in the intravascular pressure pullback data is determined.

In an embodiment, the co-registration is used to determine further information about the vessel of interest by comparing the pullback data as obtained by the two modalities and by identifying disparities between them, which are considered as indications for particular vessel characteristics specific to the vessel of interest or the blood flow therethrough.

The co-registration may particularly be performed using similarity measures, for example cross-correlation, mutual information about both pullback datasets or a lesion detection method.

One particular way of co-registering both pullback datasets is a correlation of the length of a simulated pullback curve derived from the simulated pullback data and the length of an intravascular pullback curve derived from the intravascular pullback data.

In this context, the term pullback curve refers to an illustration of the simulated and intravascular pullback data as a function of the respective simulated and intravascular pullback length. As such, in case the intravascular pullback curve is illustrated for all values obtained during the pullback recording, the length of the intravascular pullback curve corresponds to the intravascular pullback length. Else, the length of the intravascular pullback curve may correspond to an interim intravascular pullback length during which pullback recording of a first value to a final value that are represented by the pullback curve was performed.

To that end, the co-registering may be performed by assuming that the length of the intravascular pullback curve may correctly be derived from the pullback length. Upon determination of the length of the intravascular pullback curve, a spline-based length variation is used on the length of the simulated pullback curve to adjust the length of the simulated pullback curve to match the length of the intravascular pullback curve. By means of this adjustment of the lengths of the pullback curves to one another, the determination of the disparities between both modalities may be improved.

In the context of the invention, these disparities may in particular relate to local or global mismatches between the simulated pullback curve defined by the simulated pullback data and the intravascular pullback curve defined by the intravascular pullback data. Hereby, the disparities may be determined by comparing both pullback curves with one another and identifying e.g. a local minimum in the intravascular pullback curve which is not present in the simulated pullback curve.

The thus identified disparities may subsequently be output for further evaluation. In that context, the output of the identified disparity shall be understood as an output of at least one information about the identified disparity. In this case, the information may hereby be output to a user, which, upon receiving the output, may determine respective further information from the output information about the disparity. Hereby, the further information may in particular be related to inaccuracies in the physiological model, such as irregularities in the blood flow represented by the fluid dynamics model or inaccuracies in the geometry of a vessel segment of the vessel of interest as represented by a geometric model comprised in the physiological model. That is, the user may conclude that the disparity has been caused by said inaccuracies.

In an embodiment, the at least one disparity may also be output to a further processing unit which automatically derives, from the identified disparity, the further vessel information which may be related to inaccuracies in the geometric model or the fluid flow model. More particularly, co-registration unit may be configured with a further processing module to automatically determine, based on the identified disparity, said vessel information.

To that end, the co-registration unit may also be provided with a processing unit for determining said vessel information directly from the identified disparity prior to output. In this case, the co-registration unit may output the at least one vessel information determined from the identified disparity. Alternatively or additionally, the co-registration unit may be configured to output the information about the identified disparity along with the vessel information.

In an embodiment, the vessel information may be used to provide a more thorough assessment of the vessel of interest and, therefore, of the potential coronary disease. This further allows for improved treatment planning.

According to an embodiment, the at least one diagnostic image is obtained using X-ray angiography. Alternatively or additionally, the intravascular pullback curve data is obtained using a pullback recording of the Fractional Flow Reserve (FFR) or instantaneous Wave-Free Ratio (iFR).

X-ray angiography is a medical imaging technique particularly well-suited to visualize blood vessels in the (human) body. X-ray angiography is typically performed by injecting a contrast agent into the blood vessels and subsequently irradiating the body part with the contrast agent-filled blood vessels with X-ray radiation to obtain one or more two-dimensional images in which the contrast agent-filled blood vessels are clearly visible.

In an embodiment, the diagnostic image may be a two-dimensional (2D) angiographic image of the coronary vessels of the patient comprising at least one vessel of interest. The diagnostic image may also be a three-dimensional (3D) angiographic image derived from two different projections acquired using X-ray angiography.

In order to obtain a sufficiently well-resolved physiological model, the angiographic image should hereby have sufficient contrast agent filling. Furthermore, the degree of foreshortening and overlap in the angiographic image should be sufficiently low. This increases the quality of the angiographic image and subsequently simplifies the generation of the physiological model.

Instantaneous Wave-Free Ratio (iFR) refers to an invasive method for functional stenosis assessment. Particularly, an iFR acquisition is performed using a high fidelity pressure wire which is introduced into the blood vessels to be assessed. The pressure wire is then slowly pulled from a distal to a proximal end of the vessel. During pullback, pressure values are recorded as the hemodynamic parameter values, i.e. the hemodynamic parameter in this case corresponds to the (blood) pressure.

iFR acquisition is hereby performed during a specific period in diastole, which is called the wave-free period. iFR acquisition uses the ratio of the distal coronary pressure (Pd) to the pressure observed in the aorta (Pa) during the wave-free period. During this period, the waves that affect coronary flow are dormant, which means that pressure and flow are linearly related during this period. This enables an assessment of the ratio without the necessity of increasing the blood flow by means of vasodilatory agents.

According to a further embodiment, the apparatus further comprises a modeling unit configured to receive the at least one diagnostic image of the vessel of interest, to segment the diagnostic model of the vessel of interest and to generate the physiological model on the basis of said segmenting, wherein the physiological model comprises a fluid dynamics model representing fluid dynamics through said vessel of interest. The apparatus further comprises a determination unit configured to determine the simulated pullback data on the basis of said fluid dynamics model.

Accordingly, the physiological model is obtained from at least one diagnostic image of the vessel of interest. In particular, the physiological model may be obtained from a single diagnostic image of the vessel of interest. Even more particularly, the diagnostic image may be a single two-dimensional (2D) angiographic image of a vessel of interest. The diagnostic image is received by a modeling unit which generates the physiological model from said diagnostic image.

The generating of the physiological model may comprise a segmentation of the imaged vessel of interest. Thus, in the context of the invention, the segmenting the diagnostic image of the vessel of interest corresponds to segmenting the vessel of interest represented in the diagnostic image into respective vessel segments.

Based on this segmentation, a physiological model may be generated representing one or more vessel segments of the vessel of interest. To that end, the physiological model may in particular comprise a fluid dynamics model to simulate the fluid flow, i.e. the blood flow, through the respective segments of the vessel of interest.

The fluid dynamics model may particularly be generated by performing calculations that simulate the interaction of the blood with the vessel wall, i.e. the inner surface of the vessel through which the blood is flowing. These interactions are hereby defined by certain boundary conditions that take account of the properties of the vessel, such as vessel wall composition, vessel wall elasticity and vessel impedance, bifurcations in the vessel as well as blood properties, such as blood viscosity.

Hereby, generalized boundary conditions may be used, which are similar for all patients or for particular patient groups (distinguished by age, gender, physiological condition or the like). Alternatively or additionally, patient-specific boundary conditions that have been derived for a particular patient may be used for calculation of the fluid dynamics model.

In an embodiment, the fluid dynamics model may particularly refer to a lumped parameter fluid dynamics models. In such a lumped parameter fluid dynamics model, the fluid dynamics of the vessels are approximated by a topology of discrete entities. More particularly, in the lumped parameter model the vessel impedance is approximated by a series of resistor elements while the termination of a vessel is represented by an element representing ground. Thus, a vessel tree may be represented by a topology of resistors each having a particular resistance with the representation of the vessel tree being terminated by respective ground elements. These lumped parameter models reduce the number of dimensions compared to other approaches such as Navier-Stokes or the like. Accordingly, using a lumped parameter model may allow for a simplified calculation of the fluid dynamics inside the vessels and may ultimately result in reduced processing time.

In an embodiment, the fluid dynamics model is used to determine the simulated pullback data. Thus, the fluid dynamics model is used to determine the hemodynamic parameters through the vessel of interest for the one or more vessel segments. As an example, the blood pressure may be determined from the fluid dynamics model.

A simulated hemodynamic parameter value may be determined for each point of the fluid dynamics model of the blood flow through the vessel. More particularly, a particular vessel segment is regarded and a plurality of hemodynamic parameter values are simulated along a (virtual) longitudinal axis of said vessel segment for each point from a first point of the physiological model of the vessel segment to a last point. The plurality of simulated hemodynamic parameter values along the axis is provided as the simulated pullback data.

Accordingly, the distance from the first point of the vessel segment to the last point of the vessel segment corresponds to the length of the simulated pullback curve derived from the simulated pullback data. It shall thus be understood that the length of the simulated pullback curve may in particular correspond to the length of a vessel segment of the physiological model.

In an even further embodiment, the apparatus further comprises a calculation unit adapted to calculate a first representation of the simulated pullback data and a second representation of the intravascular pressure pullback data and a display unit adapted to jointly display the first representation and the second representation together with the at least one vessel information.

In the context of the invention, the co-registered simulated pressure pullback data and the intravascular pressure pullback data may be displayed to the user. This allows for a more intuitive illustration of the conformities and the difference between the pullback data obtained by the two modalities. A display unit may hereby be any unit capable of displaying a graphical representation of the data, such as a computer screen, a TV screen or the like.

The co-registered simulated pullback data may particularly be displayed as two graphs representing the simulated and intravascular pullback curves as functions of the pullback length, respectively. That is, the graphs may represent the hemodynamic parameter values from both, the simulated and intravascular pullback data, as functions of a longitudinal axis from a distal end of the vessel to a proximal end of the vessel. Even more particularly, the display may further include a representation of the at least one disparity and/or the vessel information derived therefrom.

Alternatively or additionally, the graphs representing the hemodynamic parameter values for both, the simulated and intravascular pullback data may be displayed alongside the vessel of interest shown in the image data. Even more particularly, the graphs may be integrated into the image data obtained. Alternatively or additionally, the graphs may also be represented alongside a two-dimensional (2D) or three-dimensional (3D) illustration of a physiological model of the vessel of interest.

According to a further embodiment, the simulated pullback data comprises a plurality of simulated hemodynamic parameter values and the intravascular pullback data comprises a plurality of intravascular hemodynamic parameter values having been acquired at a plurality of intravascular positions along a longitudinal axis of the vessel of interest. The comparing the simulated pullback data and the intravascular pullback data further comprises a correlating of at least one simulated value of the plurality of simulated hemodynamic parameter values to at least one intravascular value of the plurality of intravascular hemodynamic parameter values.

In an embodiment, the simulated pullback data is particularly obtained from a physiological model generated from a single 2D image. In some occasions, foreshortening occurs in obtaining diagnostic image data. When using a single image, this foreshortening may not be visible and, thus, not be identified. In these cases, the length of the simulated pullback curve derived from the simulated pullback data may be shortened compared to the length of the intravascular pullback curve derived from the intravascular pullback data, which is considered the correct length. Accordingly, the plurality of simulated hemodynamic parameter values cannot yet properly assigned to the corresponding plurality of intravascular hemodynamic parameter values.

A correlation may therefore be performed for the plurality of simulated and intravascular hemodynamic parameter values. Hereby, each simulated value may be correlated with a corresponding intravascular value. Alternatively, only a subset of the simulated values may be correlated with their corresponding subset of intravascular values.

As a result, by means of the correlation as described, the accuracy of the comparison and, thus, the determination of the disparity is improved.

In an even further embodiment, the correlating of the at least one simulated hemodynamic parameter value to the at least one intravascular hemodynamic parameter value is performed using tracking information obtained during acquisition of the intravascular pullback data.

During pullback-recording of the intravascular hemodynamic parameter values, speed variations of the pullback may occur. This may cause a variation in the interim pullback length between one or more of the intravascular hemodynamic parameter values. Thus, it may be difficult to assign each intravascular value to its respective intravascular position inside vessel at which the intravascular value has been acquired.

In order overcome this problem, the correlation may include using tracking information. In some embodiments, tracking information may particularly be obtained by tracking the position of the measurement wire during pullback. This may be performed using a fluoroscopic recording of the position of the measurement wire. Alternatively, the tracking may be performed using electromagnetic or fiber-optic catheter tracking. Likewise, the tracking may be performed using an image based registration method, i.e. by regarding the diagnostic image and by determining the position of the measurement wire using the information that may be derived from said images.

Tracking the position of the measurement wire in particular allows for determining the intravascular position at which a respective intravascular hemodynamic parameter value has been acquired, i.e. allows a definite assignment of each intravascular value to a particular intravascular position. The tracking information may thus be provided to the input unit along with the intravascular pullback data.

As a result, the length variations in the interim pullback length between each of the intravascular values may be determined and accounted for. This, in turn, improves the correlation of the simulated and the intravascular hemodynamic parameter values. More particularly, since the intravascular values may be correctly assigned to their respective intravascular positions along the vessel, it is possible to more accurately determine from the simulated pullback data that simulated hemodynamic parameter values that correspond to the intravascular hemodynamic parameter values obtained at that particular intravascular position. Thus, using tracking information enables an even more accurate co-registration of the two modalities.

In a further embodiment, the physiological model further comprises a geometric model of the vessel of interest and a vessel length of the vessel of interest in the geometric model is adjusted based on an adjusting of a length of the simulated pullback curve derived from the simulated pullback data.

In accordance with this embodiment, the physiological model further comprises a geometric model representing the geometry of the vessel of interest. The geometric model may be a two-dimensional (2D) or three-dimensional (3D) geometric representation of the model. In a particular embodiment of the invention, the geometric model is a 2D model derived from 2D angiographic image data for which a third dimension is approximated by assuming a circular shape of the vessel.

In some cases, the single diagnostic image used to generate the physiological model may have been subject to image inaccuracies, such as foreshortening in the image. This may lead to an incorrect estimation of parts of the vessel geometry, in particular the cross section of a vessel lumen or the length of a modeled vessel of interest.

As indicated herein above, the generation of a physiological model may particularly comprise a segmenting of an imaged vessel into respective vessel segments. In that context, the term vessel length refers to the length of said vessel segment that is simulated using the geometric model.

The geometry and the fluid dynamics through each vessel segment are simulated using the geometric model and the fluid dynamics model comprised in the physiological model, respectively. In particular, the simulated pullback data is obtained along the entire longitudinal axis of a particular vessel segment. This means that the length of the simulated pullback curve corresponds to the length of the vessel segment. Since this vessel segment is geometrically represented by the geometric model, it may be understood that the length of the simulated pullback curve and the length of the geometric model correspond to one another. It shall thus be understood that the length of the simulated pullback curve may in particular indicate the vessel length of the vessel of interest within the geometric model.

In accordance with this understanding, the length variation introduced to adjust the length of the simulated pullback curve to the length of the intravascular pullback curve may also be used to correct the geometric model with respect to the simulated length of the vessel segment. More particularly, the elongation factor used to elongate the length of the simulated pullback curve may also be applied to the geometric model in order to correct the geometric model from inaccuracies due to artifacts or imaging effects in the diagnostic images. Thus, by applying the elongation, a more accurate geometric model of the vessel of interest, i.e. of the respective vessel segment, may be obtained.

According to an even further embodiment the at least one disparity comprises a scale difference between the simulated pullback curve derived from the simulated pullback data and the intravascular pullback curve derived from the intravascular pullback data. In some embodiments, the comparison between the co-registered simulated and intravascular pullback curves may reveal a difference in scale. That is, the co-registrations may show a global difference between the simulated and the intravascular hemodynamic parameter values.

More particularly, the hemodynamic parameter may refer to the pressure of the blood and the at least one disparity may comprise a scale difference between the simulated pressure pullback curve and the intravascular pressure pullback curve. Therefore, the co-registration may show that the intravascular pressure values generally exceed the simulated pressure values. The global difference may hereby typically be explained by a higher than usual hyperemic blood flow. This effect is considered an indication of an overall atypical blood flow rate in the vessel of interest. Thus, the vessel information derived from the identification of this disparity may be that the vessel of interest shows and atypical blood flow rate. This information may be used to adapt the physiological model, in particular the fluid dynamics model, accordingly to more accurately represent the blood flow through the vessel of interest. Further, this information may be used to derive a value for the blood flow rate or blood flow velocity through the vessel of interest.

In accordance with a further embodiment the at least one disparity comprises a local difference in simulated gradient of the simulated pullback curve derived from the simulated pullback data and intravascular gradient of the intravascular pullback curve derived from the intravascular pullback data, wherein the difference in the simulated gradient and the intravascular gradient may occur at any position along the vessel.

In some embodiments, the comparison between the co-registered simulated and intravascular pullback data may show a local difference in the gradient of the simulated and intravascular pullback curves around any position of the vessel, i.e. a local difference in the increase or decrease of the hemodynamic parameter value along the length of the pullback curve for the simulated and intravascular pullback data.

More particularly, the hemodynamic parameter may refer to the pressure of the blood and the gradient of the simulated and intravascular pullback curves may refer to a simulated and intravascular pressure gradient, respectively. A difference in pressure gradient may in particular indicate that an eccentric cross section in the vessel is not correctly presented in the physiological model of the vessel of interest. Even more particularly, such a local difference in pressure gradient may indicate lesion eccentricity, i.e. that a lesion cross section in the vessel is larger or smaller than represented by the vessel model. Thus, the at least one disparity may indicate the vessel information that the lesion cross section is incorrectly represented in the physiological model. This indication may be used to correct the physiological model, in particular the geometric model, accordingly.

In an even further embodiment, the at least one disparity comprises a difference in the at least one simulated value of the plurality of simulated hemodynamic parameter values and the at least one intravascular value of the plurality of intravascular pressure hemodynamic parameter values.

In some embodiments, the comparison between the co-registered simulated and the intravascular pullback curve may show a local reduction of at least one or a subset of the plurality of hemodynamic parameter values for one of the simulated pullback data along the simulated pullback curve or intravascular pressure pullback data along the intravascular pullback curve.

More particularly, the hemodynamic parameter may correspond to the pressure of the blood. The comparison may show that at least one intravascular pressure value is significantly smaller than the corresponding simulated pressure value. Such a localized pressure drop may be caused by the Bernoulli effect, e.g. behind a lesion in the vessel. More specifically, due to the Bernoulli effect, local flow turbulences in the blood flow may occur. Thus, the vessel information derived from the identified disparity may relate to local flow turbulences.

This information enables the physiological model, in particular the fluid dynamics model, to be adjusted accordingly, to more accurately represent the fluid dynamics through the segment of the vessel of interest.

According to a further aspect, a method for analyzing coronary vessels is provided. The method comprises the steps of: receiving simulated pullback data determined on the basis of a physiological model generated from at least one diagnostic image of a vessel of interest and receiving intravascular pullback data acquired in-situ from the vessel of interest. The method further includes the steps of comparing the simulated pullback data and the intravascular pullback data to identify at least one disparity between the simulated pullback data and the intravascular pullback data and of outputting the at one disparity.

In an embodiment, the method further comprises the steps of: calculating a first representation of the simulated pullback data and a second representation of the intravascular pullback data and jointly displaying the first representation and the second representation together with the at least one vessel information.

In a further aspect, a computer program for controlling an apparatus according to the invention is provided, which, when executed by a processing unit, is adapted to perform the method according to the invention. In an even further aspect, a computer-readable medium having stored thereon the computer program is provided.

It shall be understood that the apparatus for analyzing coronary vessels may be implemented by means of a processing unit and the input unit, co-registration unit, modeling unit, determination unit as well as the calculation unit may be implemented as modules in the processing unit. The functionality of these modules may in particular be implemented by means of a respective algorithm. This algorithm may in particular be implemented using a machine learning algorithm implemented on said processing unit including said modules.

It shall be understood that the apparatus of claim 1, the method of claim 11, the computer program of claim 14, and the computer-readable medium of claim 15, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

The illustration in the drawings is schematically. In different drawings, similar or identical elements are provided with the same reference numerals.

Figure 1:
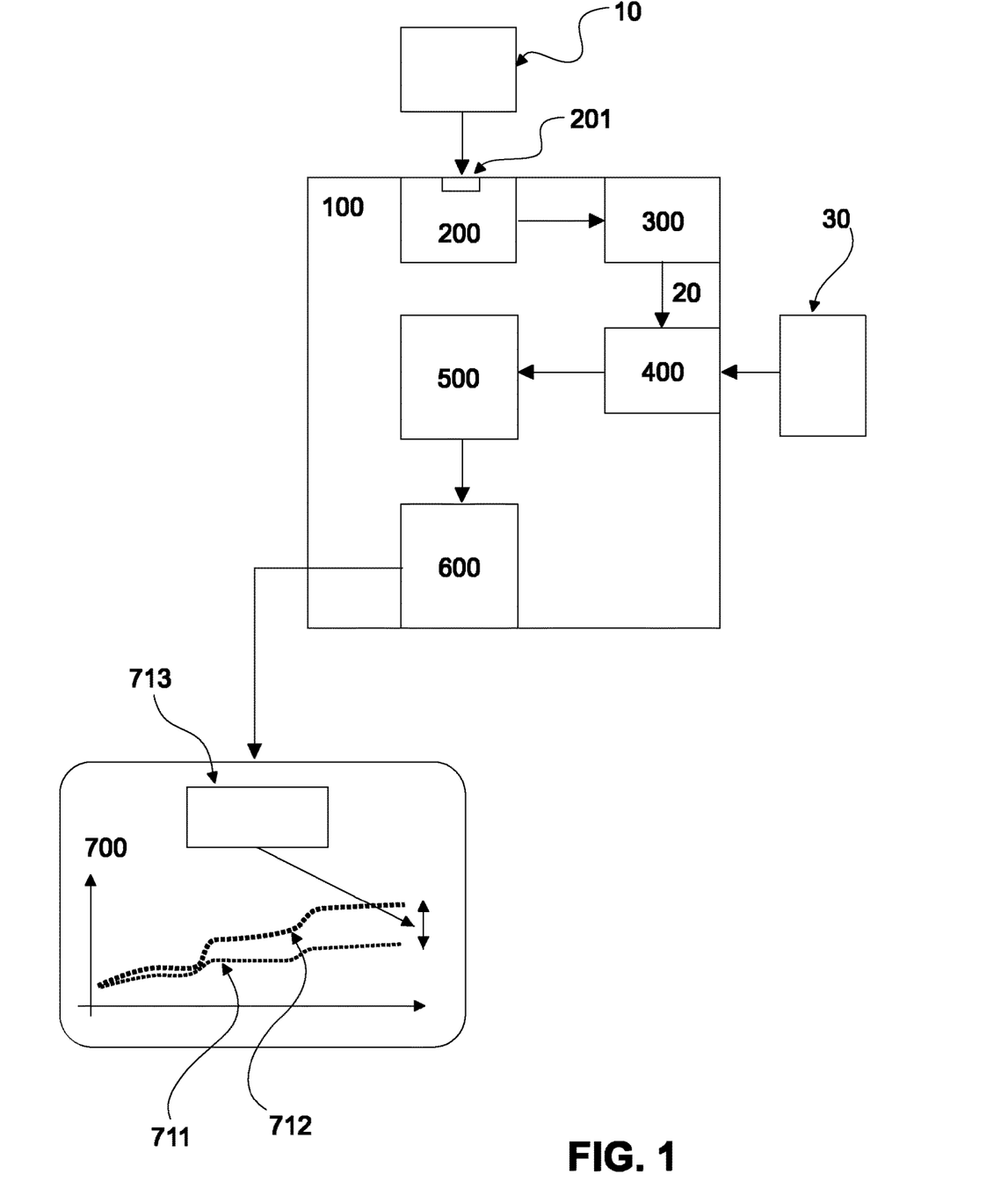
FIG. 1 schematically illustrates an apparatus for analyzing coronary vessels according to an embodiment.

FIG. 1 represents schematically an exemplary embodiment of an apparatus 100 for analyzing coronary vessels. The apparatus 100 comprises a modeling unit 200 comprising an input port 201 to receive a diagnostic image 10, which is a 2D angiographic image of the vessel of interest acquired by means of X-ray angiography. The modeling unit 200 segments the 2D angiographic image 10 to generate a physiological model comprising a fluid dynamics model.

The modeling unit 200 then provides the physiological model to determination unit 300. Determination unit 300 uses the fluid dynamics model to retrieve respective simulated pullback data 20 for the vessel of interest. In this particular embodiment, the simulated pullback data 20 corresponds to simulated pressure pullback data 20, i.e. the hemodynamic parameter regarded is the pressure of the blood.

Thus, determination unit 300 estimates, on the basis of the fluid dynamics model, a plurality of simulated pressure values for a plurality of points in the physiological model. The plurality of points hereby corresponds to a longitudinal axis of the modeled vessel of interest. That is, the simulated pressure pullback data is estimated for a particular simulated pullback length. In the embodiment, the simulated pullback length corresponds to a length of a modeled vessel segment.

The determination unit then provides the simulated pressure pullback data 20 comprising the plurality of simulated pressure values to input unit 400. Input unit 400 receives simulated pressure pullback data 20. Input unit 400 further receives intravascular pullback data 30 that has been acquired in-situ from the vessel of interest.

In this embodiment, intravascular pullback data 30 corresponds to intravascular pressure pullback data 30. More particularly, in the present embodiment, intravascular pressure pullback data 30 has been acquired using iFR pullback recording, i.e. by pulling back a pressure wire through the vessel of interest along a longitudinal axis and acquiring a plurality of intravascular pressure values at a plurality of intravascular positions. That is, the intravascular pressure pullback data is acquired for a particular intravascular pullback length.

Input unit 400 provides simulated pressure pullback data 20 and intravascular pressure pullback curve data 30 to co-registration unit 500. Co-registration unit 500 subsequently compares the simulated pressure pullback data and identifies disparities, i.e. mismatches, between simulated pressure pullback data 20 and intravascular pressure pullback data 30 acquired in-situ from the vessel of interest. Co-registration unit 500 then automatically derives a respective vessel information about the vessel of interest from the identified disparity.

Calculation unit 600 subsequently calculates first representation 711 of simulated pressure pullback data 20. Further, calculation unit 600 calculates second representation 712 of intravascular pressure pullback data 30. Finally, calculation unit 600 determines a representation 713 of the vessel information. Calculation unit 600 then provides the calculated representations to display unit 700.

In the present embodiment, display unit 700 is a screen, such as a touch screen on which one or more graphical representations may be displayed. Display unit 700 jointly displays first representation 711 and second representation 712 along with representation 713 of the vessel information derived from the disparity. In the particular embodiment according to FIG. 1, the first representation 711 and the second representation 712 displayed on the display unit are a graphical representation of the simulated and intravascular pullback curves that have been derived from the simulated and intravascular pullback data 20, 30.

Figure 2:
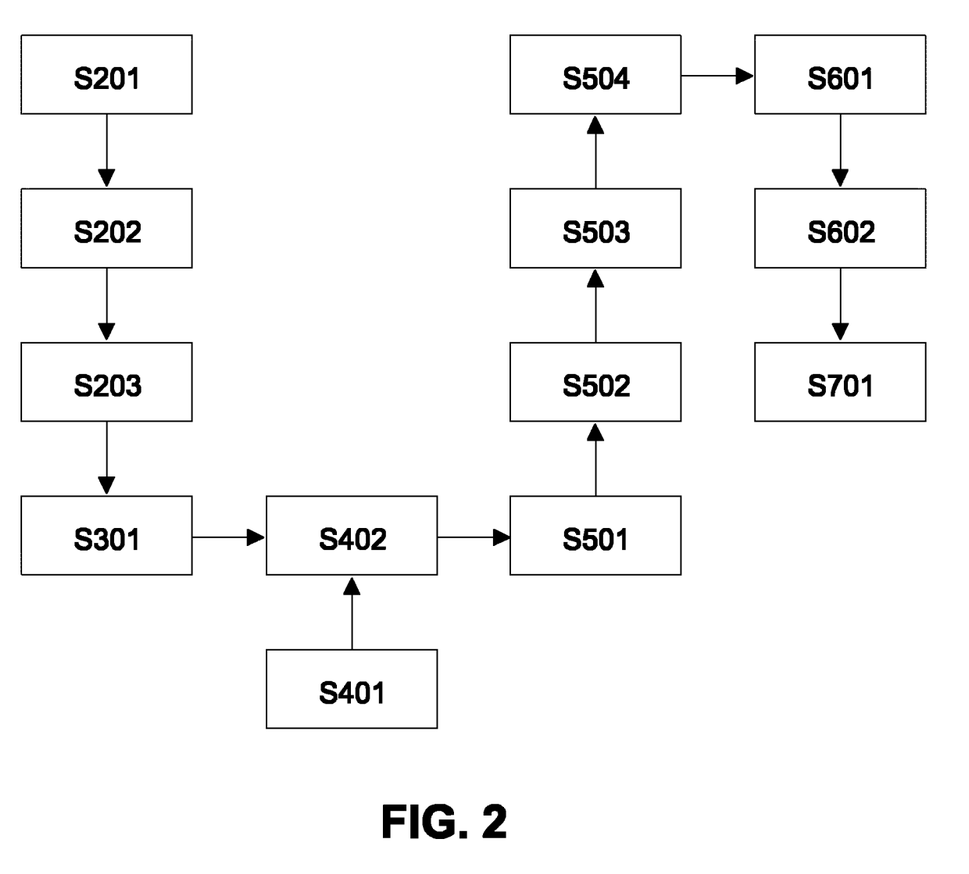
FIG. 2 represents a flow chart for a method for analyzing coronary vessels according to an embodiment.

FIG. 2 represents a flow chart for a method for analyzing coronary vessels according to an embodiment of the invention. In this embodiment, the diagnostic image 10 corresponds to a 2D angiographic image and the hemodynamic parameter obtained during pullback corresponds to the pressure of the blood.

In step S201, 2D angiographic image 10 is received at modeling unit 200. Modeling unit 200 subsequently segments the vessel of interest as shown in the angiographic image in step S202. In step S203, modeling unit 200 generates a physiological model including a fluid dynamics model and a geometric model on the basis of the segmentation and provides the physiological model to determination unit 300.

In step S301, determination unit 300 uses the physiological model, in particular the fluid dynamics model comprised therein, to determine simulated pressure pullback data 20. That is determination unit 300 uses the fluid dynamics model to simulate the blood flow through the vessel of interest. This allows an estimation of the blood pressure at different positions along the length of the modeled vessel. The thus obtained plurality of pressure values allows obtaining simulated pressure pullback data 20. Determination unit 300 provides simulated pressure pullback data 20 to input unit 400.

Input unit 400 receives, in step 402, simulated pressure pullback data 20 from determination unit 300. Further, input unit 400 receives, in step 402, intravascular pressure pullback data 30, which has been provided, in step S401, by a measurement unit used to acquire the intravascular pressure pullback data 30. Input unit 400 then provides simulated pressure pullback data 20 and intravascular pressure pullback data 30 to co-registration unit 500.

In step S501, co-registration unit 500 compares simulated pressure pullback data 20 and intravascular pressure pullback data 30. In step S502, co-registration unit 500 identifies, based on this comparison, at least one disparity between both data sets. In the present embodiment, co-registration unit 500 identifies that the length of the simulated pressure pullback curve derived from simulated pressure pullback data 20 is shorter than the length of the intravascular pressure pullback curve derived from the intravascular pressure pullback data 30 obtained in the in-situ measurement.

To that end, co-registration unit 500 uses a spline based length variation on the simulated pressure pullback curve to adjust the length of the simulated pressure pullback curve in accordance with the length of the intravascular pressure pullback curve.

In step S503, co-registration unit 500 derives a vessel information based on the identified disparity. In this case, the vessel information obtained from this disparity is related to an information about the length of the vessel segment determined from the 2D angiographic image. More particularly, the length of the simulated pressure pullback curve for simulated pressure pullback data 20 is a measure of the length of the modeled segment of the vessel of interest. Thus, it may be derived from the disparity between the length of the simulated and the intravascular pressure pullback curve by which elongation factor the geometric model of the segment of the vessel of interest may have to be corrected to more accurately represent that particular segment of the vessel of interest.

In step S504, co-registration unit 500 outputs the disparity and the vessel information derived therefrom. Further, co-registration unit 500 provides simulated pressure pullback data 20 together with information regarding the simulated pullback length and the elongation factor for elongating the length of the simulated pressure pullback curve. Further, co-registration unit 500 provides intravascular pressure pullback data 30 along with information regarding the intravascular pullback length to calculation unit 600.

In step S601, calculation unit 600 calculates a first representation 711 of simulated pressure pullback data 20. In step S602, calculation unit 600 calculates a second representation 712 of intravascular pressure pullback data 30. First representation 711 and second representation 712 are provided to display unit 700 and displayed jointly by display unit in step S701. In calculating first representation 711, calculation unit 600 considers the elongation factor for the simulated pressure pullback curve provided by co-registration unit 500 and also introduces the elongation into first representation 711.

Figure 3A:
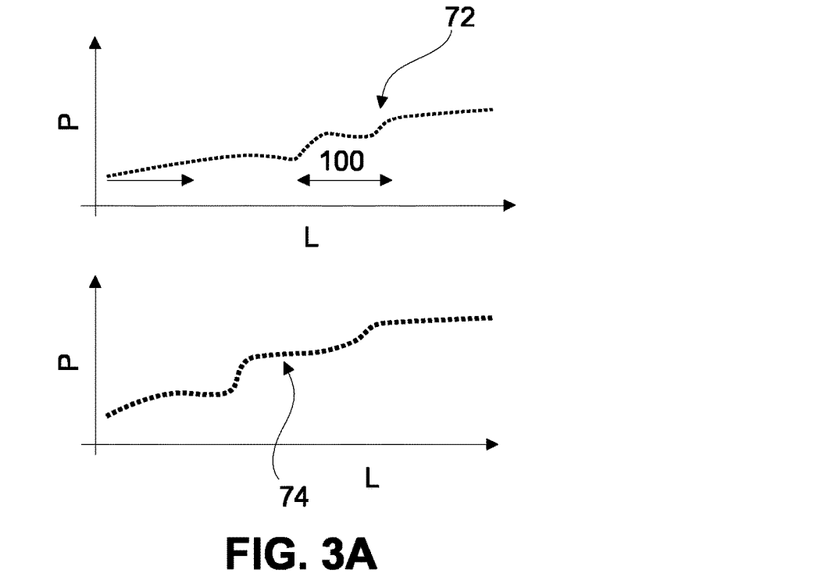
FIG. 3A shows a graphical illustration of the simulated pullback data and the intravascular pullback data according to an embodiment.

In order to more clearly understand the process of adapting a length variation during co-registration, FIG. 3A is presented. In this particular embodiment, the hemodynamic parameter considered is the pressure of the blood.

To that end, FIG. 3A shows simulated pullback curve 72 as derived for simulated pressure pullback data 20 and intravascular pullback curve 74 as derived for intravascular pressure pullback data 30. It shall be understood that pullback curves 72 and 74 are presented herein for illustrative purposes of the processes performed by the co-registration unit only.

More particularly, simulated pullback curve 72 corresponds to a graphical illustration of simulated pressure pullback data 20 as a function of the simulated pullback length prior to elongation. Simulated pressure pullback data 20 hereby comprises a plurality of simulated pressure values, which have respectively been determined at a plurality of points in the physiological model of the vessel segment. The distance of a first one of the plurality of points to a final one of the plurality of points hereby represents the length of simulated pullback curve 72. As such, the length of simulated pullback curve 72 corresponds to the length of the vessel segment. Hereby, simulated pullback curve 72 presents the pressure value ("P") as a function of the simulated pullback length ("L") along a segment of the vessel of interest going from a starting point at the distal end of the vessel to an ending point at the proximal end.

Likewise, intravascular pullback curve 74 corresponds to a graphical illustration of intravascular pressure pullback data 30 ("P") as a function of the intravascular pullback length ("L"). More specifically, intravascular pressure pullback data 30 comprises a plurality of intravascular pressure values that have been determined at a plurality of intravascular positions along the longitudinal axis of the vessel of interest.

The plurality of intravascular positions hereby comprises a starting position which may be considered the first intravascular position at the distal end of the vessel segment of the vessel of interest that has been simulated by the physiological model. Accordingly, the starting position is defined as the intravascular position at which the intravascular pullback recording of the pressure values was started for the particular vessel segment. Further, the plurality of intravascular positions comprises an ending position at the proximal end of the vessel segment, at which the recording was terminated for that particular vessel segment.

The distance along the longitudinal axis of the vessel segment from the starting position to the ending position is considered as defining the length of the intravascular pullback curve.

As may be appreciated from FIG. 3A, the progression of simulated pullback curve 72 and the progression of intravascular pullback curve 74 do not correspond to one another. More particularly, the lengths of the first and second section in simulated pullback curve 72 appear to mismatch the lengths of the corresponding sections in intravascular pullback curve 74. Even more particularly, the length of the second section in simulated pullback curve 72 appears to be shortened compared to the corresponding section in intravascular pullback curve 74. In this embodiment, this length of the second section defines the simulated pullback curve for the vessel segment to be regarded.

Since the same vessel segment is regarded in the model and the intravascular measurement of the vessel of interest, the starting point in the simulated pullback curve for the vessel segment should correspond to the above-defined starting position in the intravascular pullback curve obtained for the in-situ recording of pressure values in the particular vessel segment. Likewise, the ending point in the simulated pullback curve for the vessel segment should correspond to the ending position of the recorded intravascular pullback curve performed in the vessel segment, i.e. to the point at which the recording of pressure values in the particular vessel segment is terminated. Thus, an adjustment has to be performed to achieve the same length in both pullback curves 72, 74 for said vessel segment.

Since the length of intravascular pullback curve 74 has been obtained from a measurement, it can be assumed that the length of the second section as represented by intravascular pullback curve 74 has been correctly determined. Accordingly, the length of the second section in simulated pullback curve 72 has to be incorrect. Such an incorrect estimation of the length of simulated pullback curve 72 may occur due to inaccuracies in the diagnostic image. In the particular embodiment of FIG. 3A, the length of simulated pullback curve 72 is too short because of foreshortening in the 2D angiographic image, which could not be identified from the selected angle of the image.

Since the length of the second section in intravascular pullback curve 74 is assumed to be correct, a spline based length variation is performed on the second section of simulated pullback curve 72 to adjust the length of this section to the length of the corresponding section in intravascular pullback curve 74. That is, the second section of simulated pullback curve length is elongated, such that the starting point and the ending point of this section in simulated pullback curve 72 correspond to the starting and ending position of the respective section in intravascular pullback curve 74, respectively. This elongation is represented by the left-right arrow 100 in FIG. 3A. The thus co-registered pullback curves 73, 74 allow to further compare their respective plurality of pressure values with one another.

Figure 3B:
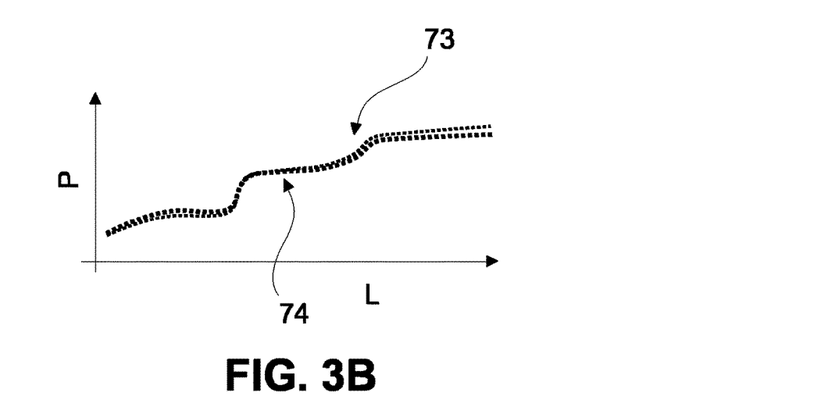
FIG. 3B shows a graphical illustration of a comparison of the simulated pullback data and the intravascular pullback data.

To that end, FIG. 3B shows an illustration of such a comparison of adjusted simulated pullback curve 73 and intravascular pullback curve graph 74 after adjustment of simulated pullback curve 72. As may be appreciated from FIG. 3B, by means of the elongation, it is ensured that each of the plurality of simulated pressure values represented by pullback curve 73 and each of the plurality of intravascular pressure values represented by pullback curve 74 provided at the same position along the length of the vessel segment correspond to each other.

Further, by means of the elongation, vessel information may be derived to correct the geometric model of the vessel. This correction may take account of inaccuracies in the 2D angiographic image from which the physiological model including the geometric model and the fluid dynamics model has been generated.

Figure 3C:
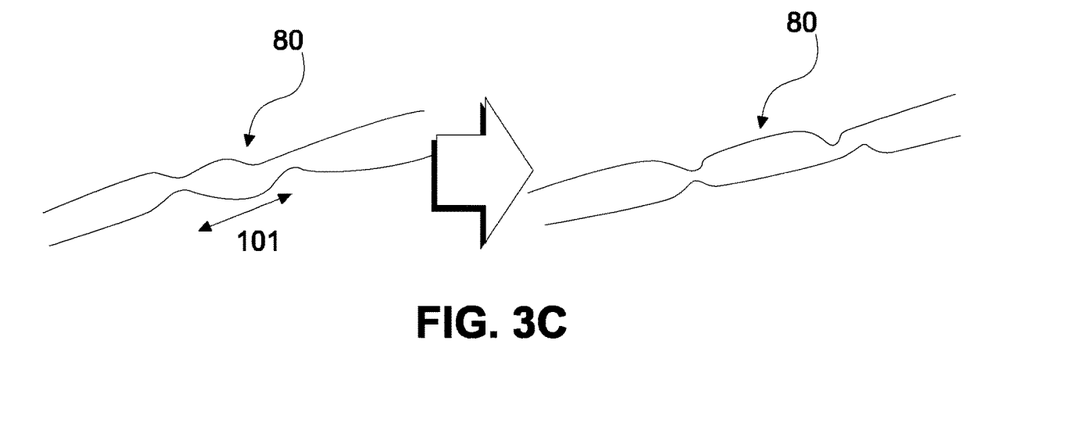
FIG. 3C shows an illustration of a correction of the geometric model on the basis of the information obtained from the co-registration of the simulated pullback data and the intravascular pullback data.

To that end, FIG. 3C shows an illustration of a correction of the geometric model according to an embodiment. On the left hand side of FIG. 3C, a 2D geometric model 80 of the vessel of interest as derived from the 2D angiographic image is shown. The length of the vessel segment has been incorrectly determined from the image. The co-registration of simulated pullback data 20 with intravascular pullback data 30 provides the additional information that the length of the vessel segment derived from the image is too short.

Specifically, since the length 100 of the second section in simulated pullback curve 72 is a measure for the length of the vessel segment represented by the physiological model, the disparity between the length of this section in the simulated pullback curve 72 and the length of the corresponding section in intravascular pullback curve 74 indicates that the length of the vessel segment has been incorrectly modeled. Thus, the information about the elongation factor used to adjust the length of the section in simulated pullback curve 72 is employed to adjust the length of the vessel segment in the geometric model. In FIG. 3C, this is represented by left-right arrow 101. The geometric model 81 of the thus elongated vessel segment is represented on the right hand side of FIG. 3C.

Figure 4:
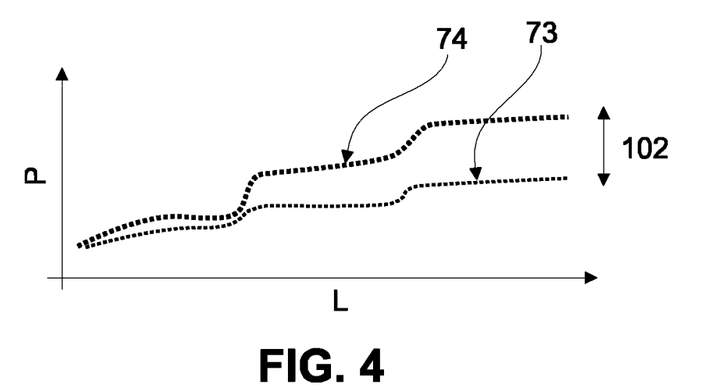
FIG. 4 shows a graphical illustration of a comparison of the simulated pullback data with the intravascular pullback data according to a further embodiment.

FIG. 4 shows an illustration of a comparison of simulated pullback data 20 with intravascular pullback data 30 after co-registration according to a further embodiment. Hereby, FIG. 4 shows simulated pullback curve 73 representing simulated pressure pullback data 20 ("P") as a function of the simulated pullback length ("L"). Further FIG. 4 shows intravascular pullback curve 74 representing intravascular pressure pullback data 30 ("P") as a function of the intravascular pullback length ("L").

Both pullback curves have hereby been derived and co-registered as described herein above. In particular, the length of the sections in simulated pullback curve 73 have been adjusted such that progression of simulated pullback curve 73 corresponds to the progression of intravascular pullback curve 74. This allows the co-registration unit to identify disparities between simulated pullback curve 73 and intravascular pullback curve 74, i.e. mismatches between simulated pullback data 20 and intravascular pullback data 30.

In the present embodiment, a comparison of both pullback curves to identify these mismatches shows that there is a difference in pressure scale between simulated pressure pullback data 20 and intravascular pressure pullback data 30. Thus, it is determined that there exists an overall difference in the magnitude of the plurality of simulated pressure values comprised in simulated pressure pullback data 20 and the magnitude of the plurality of intravascular pressure values comprised in intravascular pressure pullback curve data 30. This may be seen as an indication that there is an overall atypical blood flow in the vessel of interest.

Figure 5:
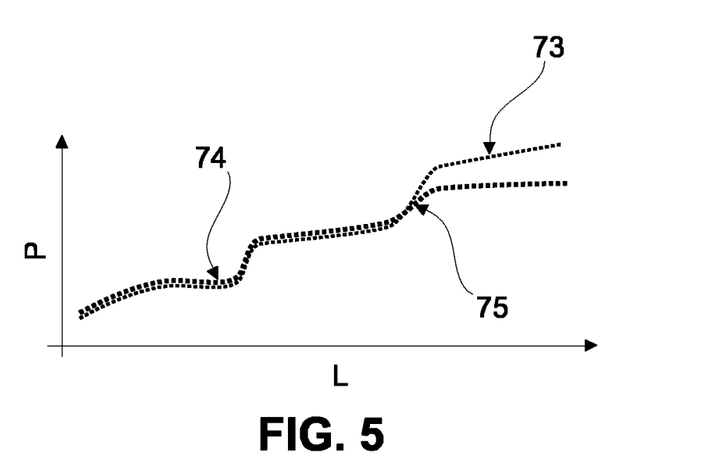
FIG. 5 shows a graphical illustration of a comparison of the simulated pullback data with the intravascular pullback data according to yet another embodiment.

FIG. 5 shows an illustration of a comparison of simulated pressure pullback data 20 with intravascular pressure pullback data 30 according to another embodiment. More specifically, FIG. 5 shows pullback curves 73 and 74, which are a representation of simulated pressure pullback curve data

20 and intravascular pressure pullback curve data 30 ("P") as functions of their respective pullback length ("L"). In this embodiment, pullback curves 73 and 74 are compared in the same coordinate system, whereby the pullback lengths correspond to one another.

In this embodiment, a comparison of both pullback curves 73, 74 to identify disparities shows that there is a difference in proximal pressure gradient 75 between simulated pullback curve 73 and intravascular pullback curve 74. Accordingly, the comparison shows that the proximal pressure gradient for simulated pressure pullback data 20 is larger than the proximal pressure gradient for intravascular pressure pullback data 30.

This local difference in pressure gradient may be viewed as an indicator that an eccentric cross section is not correctly represented in the geometric model of the vessel. More particularly the larger proximal pressure gradient for simulated pressure pullback data 20 may indicate that the actual lesion cross section is larger than the lesion cross section simulated in the geometric model. The vessel information derived from this disparity between the pressure gradients may therefore be used to correct the geometric model.

Figure 6:
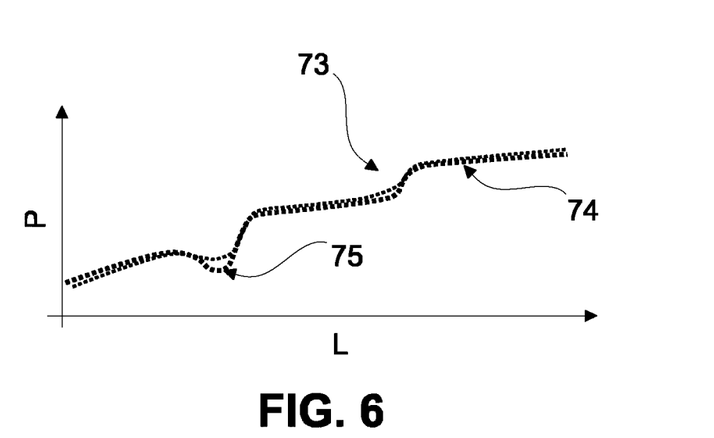
FIG. 6 shows a graphical illustration of a comparison of the simulated pullback data with the intravascular pullback data according to an even further embodiment.

FIG. 6 also shows an illustration of a comparison of simulated pressure pullback data 20 with intravascular pressure pullback data 30 according to yet another embodiment. Hereby, FIG. 6 shows pullback curves 73 and 74, illustrating simulated pressure pullback data 20 and intravascular pressure pullback data 30 ("P") as a function of their respective pullback lengths ("L").

In this embodiment, a comparison of both graphs allows to identify a locally reduced pressure value 75 in intravascular pressure pullback data 30 compared to simulated pressure pullback data 20. Such a locally reduced pressure value 75 in intravascular pressure pullback data 30 may be considered as an indication that there are local flow turbulences present in the vessel of interest at a vessel position corresponding to the intravascular position at which reduced pressure value 75 was acquired. Thus, the additional information derived from the disparity may be used to improve the estimation of the blood flow through the vessel of interest.

Although in above described embodiments, the diagnostic images have been obtained using X-ray angiography, it shall be understood that in other embodiments, the diagnostic images may be retrieved by other imaging methods, such as helical computed tomography or sequential computed tomography.

Likewise, it may be understood that the intravascular pullback data may be obtained by a method other than the instantaneous Wave-Free Ratio, such as Fractional Flow Reserve (FFR) and the resting whole cycle distal to aortic pressure ratio (Pd/Pa). Further, it may be understood that the hemodynamic parameter regarded may be a hemodynamic parameter other than blood pressure, such as hemodynamic resistance or blood viscosity or the like.

Although in the above-described embodiments, the co-registering of the simulated and the intravascular pullback data has been performed using similarity measures such as cross correlation, mutual information or lesion detection, is shall be understood that the co-registering may likewise be based on other measures. In particular, the co-registering may be fully based on fluoroscopy images or optical or electromagnetic catheter tracking. Although in the above embodiments, the deriving of the vessel information from the disparity has been performed automatically by the co-registration unit, it shall be understood that the deriving of the vessel information from the identified disparity may also be performed by a user. In particular, the deriving of the vessel information may be performed upon joint display of the co-registered pullback curves, which may include an indication of the disparity.

Further, while in the above embodiments, the analyzing has been performed on the coronary vessels, in other embodiments, the analysis may likewise be performed on vessels in other parts of the human body, such as the peripheral vessels.

It may further be understood that while in the above-embodiments, an overall difference in pressure scale, a global difference in proximal pressure gradient and a locally reduced pressure value have been identified as the respective disparity, other disparities between the pullback data may likewise be derived.

Although in the above described embodiments the vessel information derived from the identified disparity has been related to overall atypical blood flow rate, eccentric cross section and local flow turbulences, a skilled person will understand that the above described methods may likewise be used to obtain other vessel information.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the modeling of the simulated pullback data, the co-registration and comparing of the simulated and intravascular pullback data, the segmenting of the diagnostic images, the generating of a physiological model, the outputting of the identified disparity and the generation of a graphical representation, et cetera performed by one or several units or devices can be performed by any other number of units or devices. These procedures in accordance with the invention can hereby be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an apparatus for analyzing coronary vessels which comprises an input unit adapted to receive simulated pullback data determined on the basis of a physiological model generated from at least one diagnostic image of a vessel of interest, and intravascular pullback data acquired in-situ from the vessel of interest. The apparatus further comprises a co-registration unit adapted to compare the simulated pullback curve data and the intravascular pullback data to identify at least one disparity between the simulated pullback data and the intravascular pullback curve data and for outputting the at least one disparity.

The invention claimed is:

1. An apparatus for analyzing coronary vessels, comprising:
a processor comprising:
an input unit adapted to receive:
simulated pullback data comprising a plurality of simulated pressure values determined for a plurality of points in a physiological model generated from at least one diagnostic image of a vessel of interest, the plurality of points extending along a segment of the vessel of interest going from a starting point at a distal end of the vessel of interest to an ending point at a proximal end; and
intravascular pullback data comprising a plurality of intravascular pressure values acquired in-situ along the segment of the vessel of interest; and
a co-registration unit adapted to:
derive a simulated pressure curve from the simulated pullback data and an intravascular pressure pullback curve from the intravascular pullback data;
correlate a length of the simulated pullback curve with a length of the intravascular pullback curve using an elongation factor on the simulated pullback curve such that the plurality of intravascular pressure values acquired along the segment match a location of the plurality of points extending along the segment in the model;
after the correlation, compare the correlated simulated pressure curve and the intravascular pressure pullback curve to identify at least one disparity between the simulated pressure curve and the intravascular pressure pullback curve; and
output the at least one disparity.

2. The apparatus according to claim 1, wherein the at least one diagnostic image is obtained using X-ray angiography, and/or the intravascular pullback data is obtained using a pullback recording of an Instantaneous wave-Free Ratio (iFR).

3. The apparatus according to claim 1, wherein the processor further comprises:
a modeling unit adapted to:
receive the at least one diagnostic image of the vessel of interest;
segment the diagnostic image of the vessel of interest; and
generate the physiological model based on said segmenting, wherein the physiological model comprises a fluid dynamics model representing fluid dynamics through said vessel of interest;
and
a determination unit adapted to determine the simulated pullback data based on said fluid dynamics model.

4. The apparatus according to claim 1, wherein the processor further comprises:
a calculation unit adapted to calculate a first representation of the simulated pullback data and a second representation of the intravascular pullback data; and
a display unit adapted to jointly display the first representation and the second representation together with the at least one disparity.

5. The apparatus according to claim 1, wherein:
the simulated pullback data comprises a plurality of simulated hemodynamic parameter values;
the intravascular pullback data comprises a plurality of intravascular hemodynamic parameter values having been acquired at a plurality of intravascular positions along a longitudinal axis of the vessel of interest; and
the comparing the simulated pullback data and the intravascular pullback data further comprises a correlating of at least one simulated value of the plurality of simulated hemodynamic parameter values to at least one intravascular value of the plurality of intravascular hemodynamic parameter values.

6. The apparatus according to claim 5,
wherein the input unit is further configured to receive tracking information, wherein the tracking information includes information associated with one or more positions of a measurement wire during intravascular pullback; and
wherein the correlating of the at least one simulated hemodynamic parameter value to the at least one intravascular hemodynamic parameter value is performed using the tracking information obtained during acquisition of the intravascular pullback data.

7. The apparatus according to claim 5, wherein
the at least one disparity comprises a difference in the at least one simulated value of the plurality of simulated hemodynamic parameter values and the at least one intravascular value of the plurality of intravascular hemodynamic parameter values.

8. The apparatus according to claim 1, wherein the physiological model further comprises a geometric model of the vessel of interest; and wherein a vessel length of the vessel of interest in the geometric model is adjusted based on an adjusting of a length of a simulated pressure curve derived from the simulated pullback data, using the elongation factor.

9. The apparatus according to claim 1, wherein
the at least one disparity comprises a scale difference between a simulated pressure curve derived from the simulated pullback data and an intravascular pullback curve derived from the intravascular pullback data.

10. The apparatus according to claim 1, wherein
the at least one disparity comprises a difference in gradient determined from a simulated pressure curve derived from the simulated pullback data and intravascular gradient determined from an intravascular pressure pullback curve derived from the intravascular pullback data, wherein the simulated gradient and the intravascular gradient are determined at a proximal end of the vessel.

11. The apparatus according to claim 1, wherein the processor is further configured to:
output the simulated pressure pullback data, wherein the simulated pressure pullback data comprises at least one of the simulated pullback length or the elongation factor for elongating the length of the simulated pressure pullback curve.

12. The apparatus according to claim 1, wherein the elongation factor is a spline-based length variation to adjust the length of the simulated pullback curve to match the length of the intravascular pullback curve.

13. A method for analyzing coronary vessels, the method comprising the steps of:
receiving simulated pullback data comprising a plurality of simulated pressure values determined for a plurality of points in a physiological model generated from at least one diagnostic image of a vessel of interest, the plurality of points extending along a segment of the vessel of interest going from a starting point at a distal end of the vessel of interest to an ending point at a proximal end;

receiving intravascular pullback data comprising a plurality of intravascular pressure values acquired in-situ along the segment of the vessel of interest;

deriving a simulated pressure curve from the simulated pullback data and an intravascular pressure pullback curve from the intravascular pullback data;

correlating a length of the simulated pullback curve with a length of the intravascular pullback curve using an elongation factor on the simulated pullback curve such that the plurality of intravascular pressure values acquired along the segment match a location of the plurality of points extending along the segment in the model;

after the correlation, comparing the correlated simulated pressure curve and the intravascular pressure pullback curve to identify at least one disparity between the simulated pressure curve and the intravascular pressure pullback curve; and outputting the at least one disparity.

14. The method according to claim 13, further comprising the steps of:

receiving the at least one diagnostic image of the vessel of interest;

segmenting the diagnostic image of the vessel of interest; and generating the physiological model based on said segmenting, wherein the physiological model comprises a fluid dynamics model representing fluid dynamics through said vessel of interest; and determining the simulated pullback data based on said fluid dynamics model.

15. The method according to claim 13, further comprising the steps of:

calculating a first representation of the simulated pullback data and a second representation of the intravascular pullback data; and jointly displaying the first representation and the second representation together with the at least one disparity.

16. A non-transitory computer-readable medium having stored thereon a computer program, wherein, when executed by a processor, the computer program is configured to cause the processor to perform the method of claim 13.

* * * * *